United States Patent [19]

Mühlemann et al.

[11] 4,302,441

[45] Nov. 24, 1981

[54] SOLID ORAL PREPARATIONS OF UREA HYDROGEN PEROXIDE WITHOUT GLYCEROL

[75] Inventors: Hans R. Mühlemann, Beustweg 8, Zurich, Switzerland; Allen R. Firestone; Thomas Imfeld, both of Zurich, Switzerland

[73] Assignee: Hans R. Mühlemann, Zurich, Switzerland

[21] Appl. No.: 139,243

[22] Filed: Apr. 11, 1980

[30] Foreign Application Priority Data

Apr. 19, 1979 [GB] United Kingdom ............... 13619/79

[51] Int. Cl.³ .......................... A61K 7/20; A61K 9/68; A61K 31/17; A61K 33/40
[52] U.S. Cl. ........................................ 424/48; 424/53; 424/130; 424/322; 424/338
[58] Field of Search ................... 424/53, 130, 338, 48, 424/322

[56] References Cited

FOREIGN PATENT DOCUMENTS

1617430 1/1974 Fed. Rep. of Germany .
2341176 3/1975 Fed. Rep. of Germany .

OTHER PUBLICATIONS

Shapiro, W. B. et al., J. Periodontol, 1973, 44(10): 636–639 (1973), "Influence of Urea Peroxide Gel on Plaque Calculus and Chronic Gingival Inflammation.
Manhold, J. H. et al., J. Periodontol, 45(5): 312–313 (1974), "Gingival Tissue Oxygenation, Effect of Daily Application of Four Commercial Preparations".
Martindale The Extra Pharmacopoeia, pp. 1450–1451.

*Primary Examiner*—Shep K. Rose
*Attorney, Agent, or Firm*—Cushman, Darby & Cushman

[57] ABSTRACT

Solid oral preparations comprising active urea hydrogen peroxide without glycerol are effective in countering acid formed from fermentable carbohydrates in dental plaques.

16 Claims, No Drawings

SOLID ORAL PREPARATIONS OF UREA HYDROGEN PEROXIDE WITHOUT GLYCEROL

BACKGROUND OF THE INVENTION

This invention relates to solid oral preparations containing active urea hydrogen peroxide, i.e. UHP without glycerol. The term "oral preparations" comprises solid products which in the ordinary course of usage are retained in the oral cavity for a time sufficient to release urea and hydrogen peroxide in a form to effectively neutralize acids formed in bacterial agglomerates on teeth (dental plaque) and in periodontal niches.

Acids are formed in dental plaque subsequent to eating or drinking fermentable carbohydrates such as sugar in foods, beverages, snacks, desserts, sweets, confectionery, etc. Sugars, especially white refined sugar (sucrose) are known to initiate and promote dental caries especially when consumed frequently between meals. It is generally acknowledged in the field that acids formed in dental plaque from sugars (hexoses, pentoses, aldoses, ketoses) will demineralize the tooth surface and produce cavities. Acid formation in plaque occurs within a few minutes after the consumption of sugar containing food or sweets. Data have been presented by Imfeld, Th.: Proceedings of the ERGOB Conference on Health and Sugar Substitutes, Geneva, 1978, S. Karger, Basel p. 218: Subsequent to exposure to sucrose, plaque acidity 100 times higher than before exposure is recorded within 5 minutes. Hydrogen ion concentrations almost 1000 times greater are attained in 10 minutes.

Alkaline compounds, for example sodium carbonate, sodium bicarbonate, ammonium phosphates and similar ones have been suggested in the art to neutralize plaque acids in order to inhibit the cariogenic potential of dietary fermentable carbohydrates. The soapy taste of alkaline buffers has hindered their general acceptance and in addition their acid neutalizing power fades rapidly because of dilution by saliva.

Ammonium phosphate- and urea-containing dentifrices were available on the American and European markets in the fifties with claims of anticaries properties according to Cohen, A., Donzanti, A.: JADA 49: 185, 1954, which later, however, could not be confirmed, probably because of the temporal dissociation between use of dentifrice and carbohydrate consumption. Toothbrushing with toothpaste is in general, not performed immediately after meals and is usually not performed at all after consumption of snacks. The English authors Clark, R., Hay, D. I., Schram, C. J., Wagg, B. J.: Brit. D. J. 111: 244, 1961 and Gilders, B. T.: Brit. D. J. 110:17, 1961, recommended the use of sour "dental cleaning tablets" stimulating a copious flow of natural saliva. Neutralization of a sugar exposed plaque was inadequate because of the acid content of the cleaning tablets.

Liquids or gels with urea hydrogen peroxide (UHP) in general hitherto have been shown to be beneficial in treating inflammatory oral disease, such as chronic gingivitis by Pomerance, A. S., Tanchester, D.: JADA 66: 67, 1963; Rundegren, J. Fornell, J., Ericson, T.: Scand. J. dent. Res. 81:543, 1973; Kaslick, R. S., Shapiro, W. B., Chasens, A. I.: J. Periodontol. 46: 230, 1975 and Zinner, D. D., Duany, L. F., Llorente, M.: J. Prev. Dent. 5: 38, 1978 and in healing of experimental wounds by Manhold, J. H., Weisenger, E., Rustogi, K.: J. Periodontal. 45: 312, 1974. All investigators agree that the anti-inflammatory effect is mainly the result of the antibacterial action of oxygen since hydrogen peroxide alone, or chemicals not containing urea but releasing oxygen (sodium perborate, sodium peroxyborate, zinc peroxide, monoxylchlorosene) also have anti-flammatory action.

Other investigators—Brown, E. A., Cruickshank, G. A.,: J. Dent. Res. 26: 83, 1947; Shipman, B., Cohen E., Kaslick, R. S.: J. Periodontol. 42: 283, 1971; Pomerance, A. S., Tanchester, D.: JADA 66: 67, 1963; Rundegren, J., Fornell, J., Ericson, T.: Scand. J. dent. Res. 81: 543, 1973; Zinner, D. D., Duany, L. F., Chilton, N. W.: Pharmacology and Therapeutics, 1: 7, 1970; Chaconas, S. J., Newman, M. G., Newman, S. L.: IADR Kopenhagen 56, 1977, Zinner, D. D., L. F., Llorente, M.: J. Prev. Dent. 5: 38, 1978—have shown UHP in glycerol containing solutions or gels to be effective in controlling the amount of mineralized or non-mineralized dental plaque.

The reduction of mouth odor, due to thiols (Tonzetich, J., Johnson, P. W.: Arch. oral Biol. 22: 125, 1977) by oxygenating chemicals has also been reported recently by Kaizu, T., Tsunoda, M. Sato, H., Sato, T: Bull. Tokyo dent. Coll. 19: 209, 1978.

None of the above mentioned publications, however, discloses the use of active UHP, i.e. UHP not solved or contained in glycerol, in a solid preparation for the neutralization of acids formed from fermentable carbohydrates in dental plaque, i.e. in the pharmaceutical treatment of caries.

Stephan, T. M.: J. dent. Res. 22: 63, 1943 reported that the pH of "thick bacterial growths" located in the cavities of preexisting dental caries lesions is lowered by a sugar rinse (glucose) and that the decreased pH can be raised and maintained at a higher level for up to 24 hours by one subsequent 4 minute rinse with a 50 percent urea solution which had to be followed by several water rinses to remove excess urea. Concentrations in the 10 to 16 percent urea level had a much lower alkalizing potential. The observations by Stephan did not, in the last 35 years, have any dental applicability. His observations differ from the present invention in several important aspects.

(1) Stephan's experiments used urea alone to inhibit acid formation of "thick bacterial growths" located in cavities of preexisting caries lesions. The present invention proposes to use UHP for the neutralization of acid induced in plaque growing on still intact teeth. In addition, the microbiological composition of bacterial growths in carious cavities is different from the microbiology of dental placke. Long lasting inhibition of pH drops after the 50 percent urea rinse reported by Stephan have not been confirmed by other investigators. Stephan's results are explainable by soaking of the bacteria filled cavities with 50 percent urea which is not possible on smooth, intact tooth surfaces with an overlying cover of plaque; urea in rinses is in this case cleared rapidly from the oral cavity.

(2) Urea is not stable when exposed to humidity nor is it stable at 50 percent concentrations and is easily transformed into an organoleptically unacceptable, injurious product. It is possible to formulate stable oral preparations with UHP.

SUMMARY OF THE INVENTION

Urea hydrogen peroxide, $CO(NH_2)_2 H_2O_2$, is a white crystalline powder which is slowly decomposed by the humidity in the air into urea, oxygen and water. Without glycerol it is decomposed by saliva, salivary lactoperoxidases and bacterial ureases. When introduced into the oral cavity in this form it immediately starts foaming due to the action of water and salivary lactoperoxidase which liberate oxygen from the hydrogen peroxide ($H_2O_2$) moiety of UHP. Simultaneously urea is released into mixed saliva. It diffuses freely on the oral mucosa and penetrates into agglomerates of microorganisms on teeth.

In the bacterial dental plaque urea is transformed by the enzyme urease into ammonia ($NH_3$) and carbonic acid ($H_2CO_3$). Ammonia, a colorless gas, is dissolved in plaque fluid and renders resting plaque highly alkaline. Plaque acidified by previous intake of fermentable carbohydrates such as sucrose-containing foods or snacks will, due to the dissolved ammonia, shift its pH from the acid side towards neutrality. This reduction of acidity reduces the rate of tooth surface demineralization and thus the cariogenic potential of the consumed fermentable carbohydrates.

Oxygen liberated by the action of salivary lactoperoxidase also has an antiplaque and, probably, anticaries effect. This is supported by animal caries tests. Using methods described by Konig, K. G., Marthaler, T. M., Muhlemann, H. R.: Dtsch. Zahn-, Mund- u. Kieferhlk. 29: 99, 1958 the effect of topical applications of freshly prepared solutions of: hydrogen peroxide, urea, urea hydrogen peroxide, sodium percarbonate and sodium bicarbonate on incidence of plaque and fissure and smooth surface caries lesions was studied in Osborne-Mendel rats receiving tap water and a cariogenic sugar diet ad libitum. The animal caries test with 3 applications per day was conducted on 10 litters of 6 animals each, the rats being inoculated orally with S. mutans and A. viscosus at the beginning of the 20-day experimental period. The results are assembled in Table 1.

Ten percent solutions of hydrogen peroxide applied topically significantly reduced plaque and the rate of caries. Urea alone has a slight effect of borderline significance on advanced dentinal fissure lesions. UHP had a position intermediate to urea and hydrogen peroxide respectively. Alkalinization of the oral cavity with sodium bicarbonate was ineffective.

Caries reduction data for oxygen releasing sodium percarbonate are in agreement with those already reported previously by König and Mühlemann (1964).

TABLE 1

Averages per rat (N = 10) of smooth surface bacterial agglomerates (BA), initial (T) and advanced (B) dentinal fissure carious lesions, smooth surface caries units (E) and weight gains (g).

| | Treatments | BA* Plaque | T** | B** | E*** | g |
|---|---|---|---|---|---|---|
| 1 | Control, $H_2O$ | 2.7 | 10.9 | 6.0 | 13.2 | 68 |
| 2 | Hydrogen peroxide, 10%, in $H_2O$ | 0.9 | 2.0 | 0.0 | 0.3 | 70 |
| 3 | Urea, 10%, in $H_2O$ | 2.7 | 8.9 | 3.4 | 8.0 | 73 |
| 4 | Urea peroxide, 10%, in $H_2O$ | 1.3 | 5.1 | 0.4 | 4.5 | 72 |
| 5 | Sodium percarbonate, 10% in $H_2O$ | 2.0 | 8.2 | 2.6 | 2.8 | 71 |
| 6 | Sodium bicarbonate, 10% in $H_2O$ | 3.1 | 10.2 | 4.6 | 10.3 | 73 |
| $P_F$ | | 0.001 | 0.001 | 0.001 | 0.001 | NS |
| $S_{\bar{x}}$ | Standard error of the means | 0.19 | 0.65 | 0.72 | 1.22 | 2.6 |
| $S_{\bar{d}}$ | Standard error of the difference between two means | 0.28 | 0.91 | 1.01 | 1.73 | 3.7 |

TABLE 1-continued

Averages per rat (N = 10) of smooth surface bacterial agglomerates (BA), initial (T) and advanced (B) dentinal fissure carious lesions, smooth surface caries units (E) and weight gains (g).

| Treatments | BA* Plaque | T** | B** | E*** | g |
|---|---|---|---|---|---|
| two means | | | | | |

*4 units at risk
**12 fissures at risk
***20 units at risk

There is also general agreement on the lack of oral or peroral toxicity of oxygen "in statu nascendi" and of urea which is a natural constituent of blood and saliva. The effect of oxygen and oxygenating agents including urea peroxide on gingivitis, periondontitis and plaque has recently been sumarized by Gangarosa, L. P., Ross, M. M.: Pharmacology of Oxgenating Agents, Vol. 5, Pharmacology, Toxicology and Therapeutics Groups International Association for Dental Research, Washington, D.C., March 1978.

The solid oral preparation with anticarious effect and method for using the same according to this invention is specified in the claims.

In order to reduce cariogenic potential, netutralization of plaque acidity should begin within 10 minutes after having finished a carbohydrate containing snack or meal and continue until sufficient oral clearance of the carbohydrate substrate has taken place to prevent reacidification of the plaque. This is not feasible with the only available professional oral preparations containing urea, i.e. dentifrices or containing UHP in glycerol, gels, dentifrices, rinses, etc. The present discovery recommends the neutralization of acidified plaque under ambulatory conditions by means of solid oral preparations such as lozenges, tablets, chewing gums, etc. Such preparations can be manufactured in a way to release urea and hydrogen peroxide at a predetermined rate. The advantages of active UHP are unique.

(1) Oxygen is liberated by salivary lactoperoxidase. It has an antiplaque effect and the foaming action of oxygen will evenly distribute urea throughout the oral cavity.

(2) Urea is transformed into an alkalizing agent mainly in the urease-containing dental plaque, which is the target area where the cariogenic potential of carbohydrate containing foods is to be reduced.

(3) Acidic plaque can be neutralized when eating or drinking in cafeterias, restaurants, at picnics: whenever the opportunity or facilities for normal oral hygiene are not available.

In the case of chewing gum and other products, the active ingredient can be incorporated in any suitable manner during the usual manufacture of the product. For example, urea hydrogen peroxide can be incorporated in a warm gum base with stirring to distribute the same uniformly therein. The usual gum bases can be used, representative materials being jelutong, rubber latex, vinylite resins, etc. in addition to other usual materials such as plasticizers or softeners and sweeteners such as sorbitol, mannitol, xylitol etc.

The present invention is more fully described and exemplified in the examples below. It is to be understood that the invention is not to be limited to any specific form of materials or conditions set forth in the examples, but is limited solely by the description in the specifications and the appended claims. All parts are by weight unless otherwise specified. The compositions can comprise, consist essentially of or consist of the

DESCRIPTION OF THE PREFERRED EMBODIMENTS

Example 1

A compressed tablet was formed in the usual manner such that it has the following composition:

| | |
|---|---|
| Methyl cellulose | 61.95 |
| Sodium carboxymethyl cellulose | 26.55 |
| Sodium saccharinate | 0.88 |
| Flavor | 0.88 |
| Urea hydrogen peroxide | 9.74 |
| | 100.00 |

This tablet dissolves slowly in the mouth and is effective in raising the pH of interdental plaque previously acidified by consumption of fermentable carbohydrate.

Example 2

A compressed tablet was formed in the usual manner and had the following composition:

| | |
|---|---|
| Gum arabic | 55.76 |
| Ethyl cellulose | 32.53 |
| Sodium saccharinate | 0.88 |
| Flavor | 0.88 |
| Urea hydrogen peroxide | 9.95 |
| | 100.00 |

The tablet dissolves slowly in the mouth and is effective in raising the pH of interdental plaque previously acidified by consumption of fermentable carbohydrate.

Example 3

A compressed tablet formed in the usual manner had the following composition:

| | |
|---|---|
| Methyl cellulose | 44.44 |
| Xylitol | 44.44 |
| Sodium saccharinate | 0.44 |
| Flavor | 0.89 |
| Urea hydrogen peroxide | 9.79 |
| | 100.00 |

This tablet dissolves slowing in the mouth and is effective in raising the pH of interdental plaque previously acidified by consumption of fermentable carbohydrate.

That enzymes present in the saliva and plaque are capable of catalyzing the breakdown of urea hydrogen peroxide and releasing substances which can raise the pH of plaque is shown by the following in vitro test data.

A tablet as described in example 2 was added to a beaker containing 25 ml of bidistilled water (34° C.) alone or with 5 U urease or with 50 U peroxidase or with 5 U urease plus 50 U peroxidase. The breaker was placed in a mechanical incubator and shaken at 150 RPM while maintained at a temperature of 34° C. The pH of the solution was monitored with a glass pH electrode. Results of such tests are set forth in Table 2 below.

TABLE 2

| | pH of solution | | | |
|---|---|---|---|---|
| Time (min) | Water | Water + 5 U Urease | Water + 50 U Peroxidase | Water + 5 U Urease + 50 U Peroxidase |
| 0 | 5.60 | 5.75 | 5.37 | 5.42 |
| 10 | 4.89 | 6.92 | 5.08 | 7.74 |
| 20 | 4.61 | 6.39 | 4.95 | 7.05 |
| 30 | 4.47 | 6.37 | 4.88 | 6.72 |
| 40 | 4.38 | 6.58 | 4.74 | 6.66 |
| 50 | 4.34 | 6.87 | 4.63 | 6.71 |
| 60 | 4.34 | 7.02 | 4.55 | 6.91 |

Thus in presence of urease and urease plus peroxidase urea hydrogen peroxide released alkaline substances which can raise the pH of plaque.

That examples of the invention are effective in vivo in countering the acid formed in dental plaque is shown by the following test data using tablets formed as described in Example 2.

Plaque pH telemetric tests were conducted with volunteers in accordance with the procedure described previously by Imfeld in 1977. Results of such tests are set forth in Table 3 below.

TABLE 3 pH of interdental plaque in volunteers following a 2 min rinse with a 292 mM (10%) sucrose solution or after eating 20 g of chocolate pudding.

| | Sucrose | | | Pudding | |
|---|---|---|---|---|---|
| Time (min) | No tablet | 0.2g tablet 0.02g UHP | 2× (0.2g tablet 0.02g UHP) | No tablet | 2× (0.2g tablet 0.02g UHP) |
| 0 | 6.00 | 6.00 | 6.30 | 6.00 | 6.00 |
| 5 | 4.50 | 4.90 | 5.00 | 5.15 | 5.10 |
| 10 | 3.95 | 4.50* | 4.80* | 4.80 | 4.80* |
| 15 | 4.05 | 5.50 | 5.50 | 4.45 | 5.40 |
| 20 | 3.85 | 5.95 | 5.85 | 4.40 | 6.05 |
| 22 | — | 6.30** | — | — | — |
| 25 | 3.70 | 6.40 | — | 4.45 | 6.50 |
| 27 | — | — | 6.50 | 4.60 | 7.00** |
| 30 | — | — | — | 4.90 | 6.80 |
| 35 | — | — | — | — | — |
| 38 | — | — | 6.10** | — | — |
| 40 | 3.85 | — | 6.25 | 4.90 | 6.65 |

*begin tablet(s)
**tablet(s) completely dissolved

Sucrose solutions alone, or as an example of a typical snack containing fermentable carbohydrates and sugar, chocolate pudding, reduced plaque pH in human volunteers to levels generally acknowledged in the to be capable of dissolving enamel and when repeated frequently of initiating dental caries. However, when the volunteers sucked on one or two 0.2 g tablets containing urea hydrogen peroxide as given in the examples 2 through 4 the pH of interdental plaque was raised to levels generally acknowledged in the field to be safe for teeth.

Thus, it was found that the present invention raised the in vivo pH of human interdental plaque previously acidified by the consumption of fermentable carbohydrates to levels safe for teeth and maintained it at these levels over a length of time.

While the invention has been described in detail according to preferred compositions, it will be obvious to those skilled in that art that changes can be made, without departing from the spirit or scope of the invention, and it is intended in the appended claims to cover such changes and modifications.

The products of the present invention are solid oral preparations containing as agent capable of countering acid formed in dental plaque, active urea hydrogen peroxide, said agent being present in an effective amount usually up to about 15%, the preferred amount being about 10% when said agent is present in a solid oral preparation to be dissolved and/or disintegrated in the mouth.

The composition can comprise for example a soluble cellulose ether, e.g., methyl cellulose, ethyl cellulose, sodium carboxymethyl cellulose a sweetener, e.g., a sugar alcohol such as mannitol, sorbitol, or xylitol, or saccharin, e.g. in the form of sodium saccharinate, or other non-toxic salt and a carbohydrate gum, e.g. gum arabic.

The chewing gum, lozenge or tablet which is taken or administered orally contains sufficient urea hydrogen peroxide to neutralize acid plaque on the teeth.

What is claimed is:

1. A solid orally administrable composition in the form of lozenge, tablet or chewing gum for neutralizing acid in dental plaque which composition comprises as active ingredient urea hydrogen peroxide in an amount effective to neutralize said acid and up to 15% by weight and in the absence of glycerol together with a sweetner selected from the group consisting of mannitol, sorbitol xylitol and saccharin and a carrier selected from the group consisting of soluble cellulose ethers and carbohydrate gums.

2. A composition according to claim 1 which contains 9 to 11% by weight urea hydrogen peroxide.

3. A composition according to claim 1 in the form of chewing gum.

4. A composition according to claim 1 in the form of a tablet.

5. A composition according to claim 4 containing 9 to 15% by weight urea hydrogen peroxide.

6. A composition according to claim 1 wherein the sweetener is sodium saccharinate.

7. A composition according to claim 6 including at least one member from the group consisting of methyl cellulose, ethyl cellulose and sodium carboxymethyl cellulose.

8. A composition according to claim 6 including a carbohydrate gum.

9. A composition according to claim 1 in tablet form consisting essentially of

| | |
|---|---|
| methyl cellulose | about 62% |
| sodium carboxymethyl cellulose | about 26–27% |
| sodium saccharinate | about 0.9% |
| flavor | about 0.9% |
| urea hydrogen peroxide | about 10% |

10. A composition according to claim 1 in tablet form consisting essentially of

| | |
|---|---|
| gum arabic | about 55–56% |
| ethyl cellulose | about 32–33% |
| sodium saccharinate | about 0.9% |
| flavor | about 0.9% |
| urea hydrogen peroxide | about 10% |

11. A composition according to claim 1 in tablet form consisting essentially of

| | |
|---|---|
| methyl cellulose | about 62% |
| sodium carboxymethyl cellulose | about 26–27% |
| sodium saccharinate | about 0.9% |
| flavor | about 0.9% |
| urea hydrogen peroxide | about 10% |

12. A method for neutralizing acid in dental plaque comprising orally taking the composition of claim 1.

13. A method according to claim 12 wherein the composition contains 9 to 11% urea hydrogen peroxide.

14. A composition according to claim 1 in the form of a 0.2 gram tablet containing 0.02 gram of urea hydrogen peroxide.

15. A composition according to claim 1 containing up to 10% of urea hydrogen peroxide.

16. A method for neutralizing acid in dental plaque comprising orally taking the composition of claim 1 in an amount effective to release urea into the saliva and to diffuse freely on the oral mucosa and penetrate into agglomerates of microorganisms on the teeth and react with the enzyme urease to form ammonia and thereby neutralize the acid.

* * * * *